United States Patent [19]

Savitz et al.

[11] 4,229,299

[45] Oct. 21, 1980

[54] PERISTALTIC DIALYSATE SOLUTION PUMP

[75] Inventors: Steven R. Savitz, Astoria; James A. Drago, Brewster, both of N.Y.

[73] Assignee: Hoechst Aktiengesellschaft, Frankfurt, Fed. Rep. of Germany

[21] Appl. No.: 888,858

[22] Filed: Mar. 22, 1978

[51] Int. Cl.² ............................................ B01D 31/00
[52] U.S. Cl. .................................. 210/85; 210/96.2; 210/137; 210/180; 210/188; 210/321 B; 210/416 M; 417/477
[58] Field of Search .............. 210/321 B, 22 A, 96 M, 210/85, 186, 195 R, 416 M, 137, 180, 188; 417/477, 53

[56] References Cited

U.S. PATENT DOCUMENTS

| | | | |
|---|---|---|---|
| 910,125 | 1/1909 | Graser | 417/477 |
| 3,137,242 | 6/1964 | Hahn | 128/214 R |
| 3,212,642 | 10/1965 | Kylstra | 210/321 B |
| 3,216,362 | 11/1965 | Hewko | 417/477 |
| 3,722,680 | 3/1973 | Smith | 210/186 X |
| 3,878,095 | 4/1975 | Frasier et al. | 210/321 B X |
| 3,882,020 | 5/1975 | Cere | 210/85 |
| 3,976,574 | 8/1976 | White | 210/188 |
| 3,979,284 | 9/1976 | Granger et al. | 210/321 B |
| 4,079,007 | 3/1978 | Hutchisson | 210/321 B X |
| 4,083,777 | 4/1978 | Hutchisson | 210/22 A |
| 4,131,399 | 12/1978 | Calvet | 417/477 |

OTHER PUBLICATIONS

Eyoshi, et al. "Portable Artificial Kidney System Prototype," article in *Artificial Kidney-4*, as presented at the Twelfth (1974) Japanese Society for Artificial Organs Meeting, pp. 8-9.

*Primary Examiner*—Frank A. Spear, Jr.
*Attorney, Agent, or Firm*—Curtis, Morris & Safford

[57] ABSTRACT

Peristaltic pump means for pumping dialysate solution through a dialysate solution flow circuit in a hemodialysis system. The pump comprises four rollers mounted on a rotatable base member with a relatively long segment of flow circuit tubing tensionally extended around the pump head so as to be simultaneously engaged and compressed by at least two of the rollers, the rollers being mounted for longitudinal movement of the points of compression along the tubing during rotation of the pump head assembly to advance dialysate solution through the flow circuit. The disclosed pump means provides a substantially uniform dialysate solution flow rate under conditions of varying dialysate solution negative pressure and is particularly suitable for use in a unitary, portable hemodialysis module of a type adapted for coupling with either a single-pass proportioning system or a batch dialysate solution supply. A proportioning system is disclosed for such arrangement which employs a recirculating deaeration means for removal of soluble gases from the water employed for make-up of dialysate solution. The peristaltic dialysate solution pump is mounted in the portable hemodialysis module in a manner which facilitates rapid changeover from single-pass to batch dialysate solution flow, and vice versa.

18 Claims, 8 Drawing Figures

FIG. 5
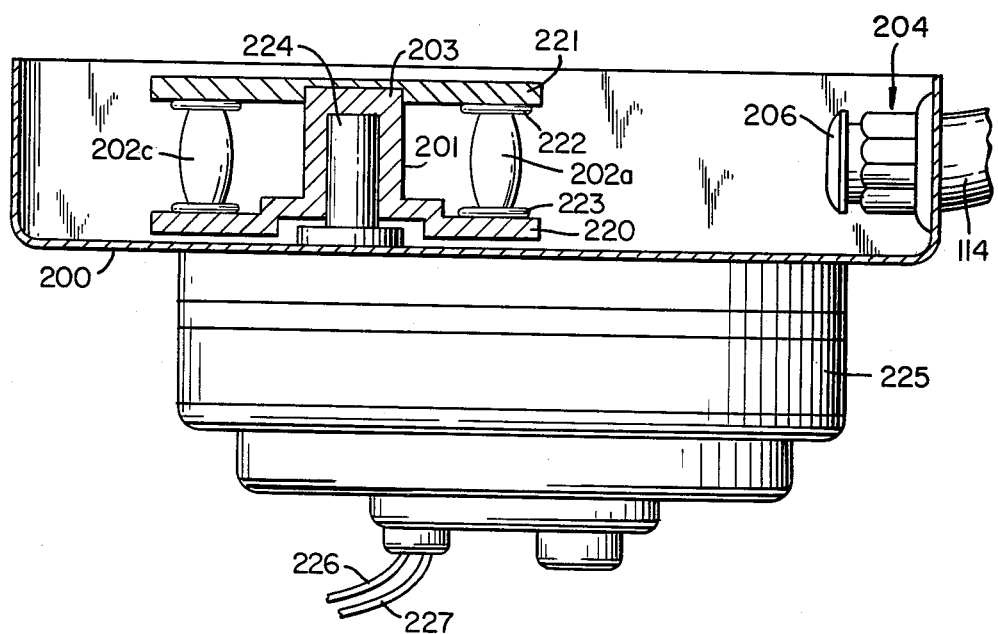
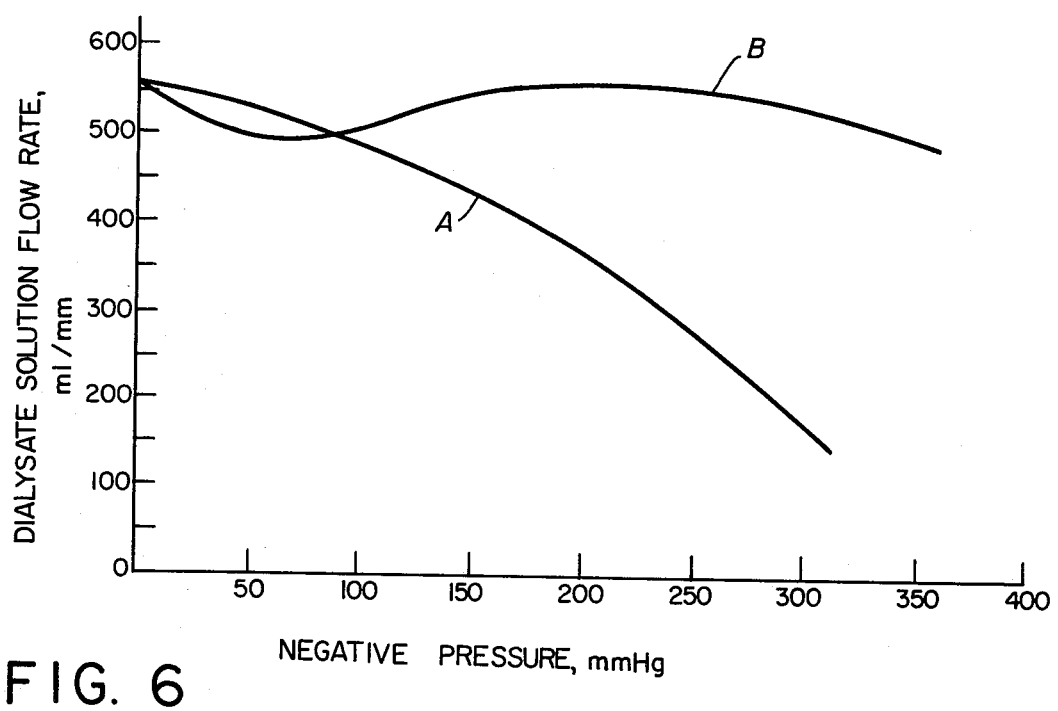
FIG. 6

PERISTALTIC DIALYSATE SOLUTION PUMP

BACKGROUND OF THE INVENTION

1. Field of the Invention

This invention relates generally to peristaltic pump means for pumping dialysate solution through a dialysate solution flow circuit in a hemodialysis system.

2. Description of the Prior Art

Hemodialysis systems have been in general use for a number of years in the treatment of renal disease and disability, and have proven highly effective in providing artificial kidney functions for persons whose own natural kidneys are functionally imparied. In operation of the hemodialysis system, blood containing waste substances such as for example urea, creatinine, excess electrolytic salts and water, is withdrawn from the body and flowed through a dialyzer in indirect mass transfer relationship with an aqueous dialysate solution. The dialyzer may be of various conventional types including a mass transfer member such as an extended surface elastomeric membrane or a hollow fiber bundle across which the waste substances are transferred by concentration gradient (solute impurities) or osmotic pressure (water) from the blood to the dialysate solution. From the dialyzer the blood which has thus been depleted in impurities is returned to the patient's body. The impurity-enriched dialysate solution from the dialyzer is either disposed of to waste or else is recirculated in a closed loop from a dialysate solution source through the dialyzer for renewed mass transfer from the blood to the dialysate solution. The dialysate solution employed in conventional hemodialysis treatment is an aqueous solution of various selected slats which provide the desired electrolytic balance with the blood in the dialyzer and thus prevent the loss of valuable blood constituents to the dialysate solution by diffusion and osmosis in the dialyzer.

In the general practice of dialysis, it is frequently desirable to operate the dialysis system such that the pressure in the dialysate solution on one side of the mass transfer member of the dialyzer, e.g., dialyzer membrane, is at a somewhat reduced (negative pressure) level relative to the pressure of the blood on the other side of the dialyzer mass transfer member. Such mode of operation provides a pressure differential across the mass transfer member of the dialyzer and is employed to facilitate the transport of excess water from the patient's circulatory system to the dialysate solution flow stream by osmotic pressure flow. This removal of excess water, commonly referred to as ultrafiltration, usefully provides a means for removal of water from the patient's body, such as would ordinarily be carried out with the aid of functional natural kidneys.

It is taught by the prior art to employ in the hemodialysis system a dialysate solution flow circuit including a flexible resilient tubing pumping section through which dialysate solution is pumped by peristaltic pump means having a plurality of circumferentially spaced-apart rollers mounted on a rotable base member. In such system, the flexible resilient tubing pumping section is tensionally extended around the rollers so as to be simultaneously engaged and compressed by at least two of the rollers, with the rollers being mounted for longitudinal movement of the points of compression along the tubing during rotation of said pump base member to advance dialysate solution through the tubing.

A recently developed dialysate solution peristaltic pump of the above-described type is disclosed and claimed in U.S. Ser. No. 720,672, now U.S. Pat. No. 4,083,777, filed Sept. 7, 1976 in the name of J. T. Hutchisson. This pump is highly efficient and extremely small in size and weight. For such reasons, this prior art pump has been employed and is particularly suitable for use in portable hemodialysis systems. More specifically, the pump disclosed in Ser. No. 720,672 comprises three rollers mounted on a base member, each roller having a diameter of between 0.25 and 0.75 inch and circumferentially spaced apart at an angle of 120° from the other rollers with a radial distance between the roller axis and pump head assembly base member fixed axis of from 0.50 to 1.25 inches. This prior art pump employs a flexible resilient tubing pumping section having a length, as measured longitudinally along the tubing between the anchored end segments thereof, of from 6.0 to 6.75 inches, a wall thickness of from 0.03 to 0.10 inch and an internal diameter of from 0.18 to 0.25 inch, with drive means connected to the pump head assembly for rotation thereof at a speed in the range of from 200 to 600 rpm.

Despite the advantages of high efficiency and small size and weight of the dialysate solution pump disclosed in U.S. Ser. No. 720,672, it has been found that the output flow rate of dialysate solution provided by this prior art pump varies drastically with changes in negative pressure in the dialysate solution. Such flow rate-negative pressure characteristic represents a severe operating disadvantage for the prior art pump when employed to pump dialysate solution in the hemodialysis system, for the reason that it is generally necessary to vary the level of negative pressure of the dialysate solution being pumped through the dialyzer in such system from patient to patient and, for a given patient, from dialysis to dialysis, depending on the level of ultrafiltration water removal required in a particular dialysis treatment. For example, the effect of increasing the dialysate solution negative pressure for dialysis is to correspondingly increase the pressure gradient driving force for mass transfer of water from the blood through the dialyzer mass transfer surface to the dialysate solution passed in indirect mass transfer dialyzing relationship with the blood, so as to insure complete removal of water from the blood in the course of dialysis treatment. The above-described prior art pump of U.S. Ser. No. 720,672 responds to increased negative pressure with drastically reduced output flow of dialysate solution from the pump. The resulting reduction in dialysate solution flow rate in the dialysate solution flow circuit of the hemodialysis system adversely affects the overall efficiency of the dialysis treatment and requires significantly increased treatment time to effect the required removal of inpurities from the blood being dialyzed.

Faced with the problem of widely varying dialysate solution flow rate from a single peristaltic pump with changes in dialysate solution negative pressure, the prior art has proposed various arrangements in which two peristaltic pumps are disposed in series in the dialysate solution flow circuit to maintain relatively constant flow therein despite changes in dialysate solution negative pressure. In one such arrangement, a first peristaltic pump is disposed upstream of the dialyzer, with a flow restriction device interposed between the first peristaltic pump and the dialyzer to create negative pressure in the dialysate solution flowing therethrough. A second peristaltic pump is disposed downstream of the dialyzer.

The function of the second pump is to accommodate the variation in dialysate solution flow rate from the first pump with changes in negative pressure, i.e., to "smooth" the output flow rate from the first pump, so as to maintain a substantially constant flow rate in the dialysate solution flow circuit despite such negative pressure changes. Although the dual peristaltic pump arrangement is effective in overcoming the problem of variance in dialysate solution flow rate with changes in dialysate solution negative pressure, such arrangement involves the added expense and complexity of a second peristaltic pump as compared to hemodialysis systems wherein only single peristaltic pump means are employed.

Accordingly, it is an object of this invention to provide improved peristaltic pump means for pumping dialysate solution through a dialysate solution flow circuit in a hemodialysis system.

It is another object of the present invention to provide a single peristaltic pump means capable of delivering a substantially constant output flow rate of dialysate solution despite changes in the negative pressure of the dialysate solution being pumped.

Other objects and advantages of the invention will be apparent from the ensuing disclosure and appended claims.

SUMMARY OF THE INVENTION

This invention relates generally to peristaltic pump means for pumping dialysate solution through a dialysate solution flow circuit in a hemodialysis system.

Briefly, the invention relates to a hemodialysis apparatus for treatment of blood to remove waste impurities therefrom. The apparatus includes dialyzer means through which waste impurity-containing blood and a dialysate solution are passed in indirect mass transfer dialyzing relationship for transfer of the waste impurities from the blood to the dialysate solution. Means are provided for transferring waste impurity-containing blood from a patient to the dialyzer means and for returning waste impurity-depleted blood to the patient. Means are also provided for transferring dialysate solution from a dialysate solution source to the dialyzer means along with means for discharging waste impurity-enriched dialysate solution from the dialyzer means forming a dialysate solution flow circuit including a flexible resilient tubing pumping section through which dialysate solution is pumped. Peristaltic pump means are employed with a rotatable pump head assembly including a base member positioned for rotation about a fixed axis with a plurality of circumferentially spaced apart rollers mounted thereon for independent rotation about respective axes parallel to the base member fixed axis. Means are provided for anchoring the end segments of the flexible resilient tubing pumping section such that the tubing is tensionally extended around the pump head assembly, being simultaneously engaged and compressed by at least two of the circumferentially spaced apart rollers, the rollers being mounted for longitudinal movement of the points of compression along the tubing during rotation of said pump head assembly to advance dialysate solution through the tubing.

In accordance with the specific improvement of this invention, the peristaltic pump means comprises four rollers mounted on the base member, each having a generally convex surface profile, for only partial closure of the tubing at the points of compression by the rollers, with a maximum diameter of between 0.25 and 0.75 inch and circumferentially spaced 90° apart from adjacent rollers with a radial distance between the roller axis and said base member fixed axis of from 0.50 to 1.50 inches. The flexible resilient tubing pumping section has a length, as measured longitudinally along the tubing between the anchored end segments thereof, of from 6.75 to 11.0 inches, a wall thickness of from 0.07 to 0.125 inch, and an internal diameter of from 0.18 to 0.35 inch. Drive means are coupled to the pump head assembly for rotation thereof at a speed in the range of from 50 to 400 rmp.

DESCRIPTION OF THE DRAWINGS

FIG. 5 is a sectional elevational view of the dialysate solution pump of FIG. 4, together with associated drive means.

FIG. 6 is a graph of dialysate solution flow rate, in ml/min. plotted as a function of negative pressure of the dialysate solution, in mm Hg, showing performance curves for the dialysate solution pump of FIGS. 4-5 and a dialysate solution pump according to the prior art.

BRIEF DESCRIPTION OF THE PREFERRED EMBODIMENTS

Figure 1:
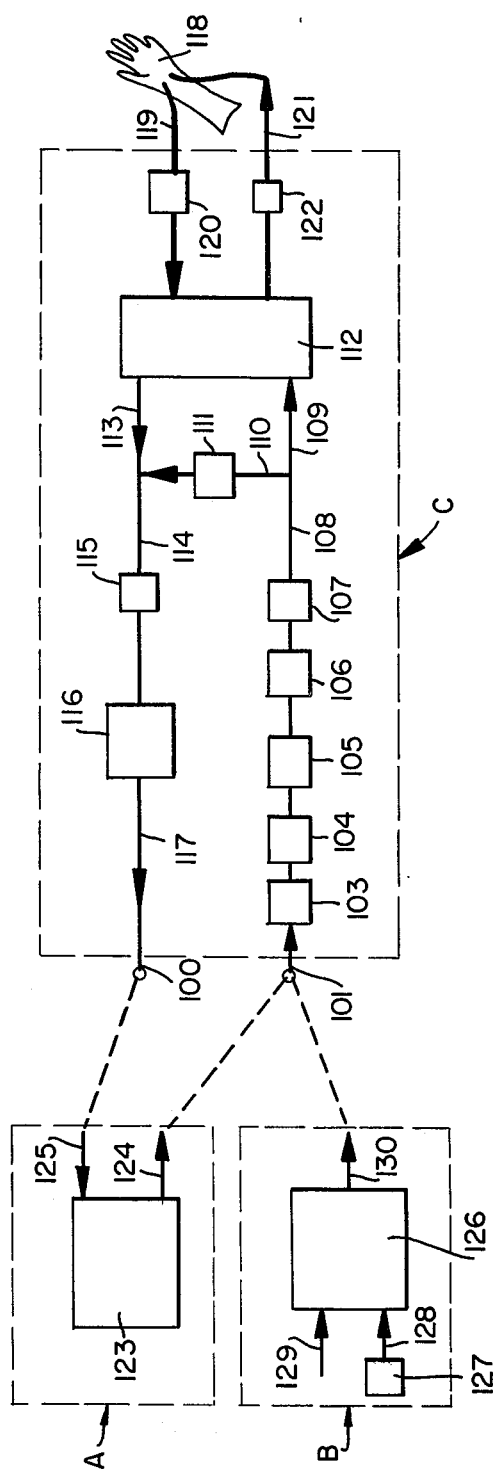
FIG. 1 is a schematic block diagram of a hemodialysis system such as may be usefully employed in connection with the practice of the present invention.

Referring now to the drawings, FIG. 1 shows a schematic block diagram of a hemodialysis system such as may be usefully employed in connection with the practice of the present invention. In this illustrative system, the patient or hemodialysis subject 118 is joined in a closed loop blood flow circuit formed by blood flow tubing segments 119 and 121 with dialyzer means 112, which may be of any suitable conventional type, as for example a parallel plate or hollow fiber bundle types. Waste impurity-containing blood is withdrawn from the patient as by means of an arterial fistula, cannula or shunt (not shown) and transferred by tubing segment 119 to peristaltic blood pump means 120 located upstream of the dialyzer means 112. By means of the blood pump 120, the withdrawn waste impurity-containing blood is peristaltically pumped to advance blood through the above-described blood flow circuit. The blood pump 120 may suitably be of a type as disclosed and claimed in U.S. patent application Ser. No. 720,672 filed Sept. 7, 1976 in the name of J. T. Hutchisson. The speed of the peristaltic blood pump may suitably be controlled by a motor speed control device coupled therewith, to obtain the necessary flow rate of blood through the blood flow circuit, as for example about 200 milliliters per minute.

After being pumped by the peristaltic blood pump means 120, the waste impurity-containing blood is passed via line 119 through the dialyzer means 112 in indirect mass transfer dialyzing relationship with the dialysis solution entering the dialyzer in line 109. As mentioned, the dialyzer means may suitably be of the parallel flow hollow fiber type comprising a bundled array of hollow fibers through which the waste impurity-containing blood is passed in countercurrent flow relationship with the dialysate solution flowing through the bundled array along the exterior surfaces of the hollow fibers. Waste-impurity depleted blood is returned from the dialyzer means to the patient by blood return line 121. The blood return line has an air leak detector means 112 associated therewith to indicate the presence of any gas bubbles in the blood being returned to the patient. The detector means 122 may suitably be coupled with an output visual display device or audio alarm means to alert the patient to the presence of gas bubbles in the return blood stream and, in addition, the detector means may be operatively coupled with clamping means (not shown) which function to clamp the return blood line 121 when air is detected in the blood by the detector means 122, such that the partially clamped blood return line prevents any gas from being returned with the blood to the patient's body.

As shown, the hemodialysis system shown in FIG. 1 is separated into three discrete portions, each enclosed by a dashed line and representing a discrete module of the overall hemodialysis system. Portion "C" of FIG. 1 represents the hemodialysis module of the overall hemodialysis system. Portions "A" and "B" represent alternative sources of dialysate solution for the hemodialysis module "C". Portion "A" represents a dialysate solution batch recirculation module, comprising a dialysate solution source container 123 provided with outlet and return lines 124 and 125 respectively. As indicated by the drawing, the inlet and return lines of the batch recirculation module may be interconnected with the dialysate solution flow circuit in the hemodialysis module "C" by means of connector means 100 and 101. In this fashion, a closed loop dialysate solution flow circuit is formed, with dialysate solution from container 123 being introduced in line 124 into line 102 for eventual flow through the dialyzer 112, and with waste impurity-enriched dialysate solution being discharged from the hemodialysis module "C" in line 117 coupled by connector means 100 to line 125 for return of the dialysate solution to the source container 123 thereof. Alternatively, the proportioning module "B" can be coupled with hemodialysis module "C" to provide an open loop, singlepass flow dialysate solution flow circuit. The proportioning module "B" includes a proportioning system 126 which receives a continuous flow of water in line 129 from any suitable source means. In the proportioning system 126 water from line 129 and a dialysate concentrate introduced to the proportioning system in line 128 from dialysate concentrate source container 127 are mixed together in a predetermined ratio to form dialysate solution for hemodialysis, which is discharged from the proportioning system in line 130. Line 130 may suitably be coupled to line 102 of the hemodialysis module "C" by connector means 101. In the open loop, singlepass mode, the terminal portion of dialysate solution discharge line 117 is suitably coupled with drain or other waste disposal means. The provision of separate dialysate solution supply modules for open loop and closed loop operation provides great versatility for the user of the hemodialysis system, particularly if the respective modules "A", "B" and "C" are designed for ready portability, inasmuch as the proportioning module "B" can be used where suitable water source supply means exit, while the batch recirculation module "A" may otherwise be employed.

Regardless of whether dialysate solution supply module "A" or "B" is employed, the operation of the dialysate solution flow circuit portion associated with the hemodialysis module "C" is the same. Dialysate solution entering the hemodialysis module "C" in line 102 is passed to heating means 103 wherein the dialysate solution is heated, if necessary, to approximately 98°–100° F. Such heating is carried out to yield a proper dialysate solution temperature to prevent undue heating or cooling of the blood by heat exchange with the dialysate solution and to prevent hemolysis. Warm dialysate solution is flowed from the heating means 103 to the dialysate solution temperature sensing assembly 104.

In the temperature sensing assembly, means are provided for sensing the temperature of the dialysate solution together with means for converting dialysate solution temperature sensing into a transmitable signal. This temperature sensing signal is transmitted by suitable transmission means to a temperature control circuit, which compares the temperature sensing signal with a set point value and generates a resulting control signal which is transmitted by suitable control signal transmitting means to the heating means 103 to provide the requisite level of heating for maintaining the set point value. In this manner, the rate of heating of the dialysate solution by the heating means is adjusted in response to the temperature sensing in the assembly 104 to maintain a predetermined dialysate solution temperature level.

In addition to the control function served by the temperature sensing signal in the temperature sensing assembly 104, the sensing signal may also be employed to actuate visual temperature display means or audio alarm means when the dialysate solution temperature exceeds allowable limits.

From temperature sensing assembly 104, the dialysate solution is passed to conductivity sensing assembly 105. In assembly 105, means are provided for sensing the electrolytic conductivity of the dialysate solution, together with means for converting the dialysate solution electrolytic conductivity sensing into a transmittable signal. The transmittable signal may be transmitted by suitable signal transmission means to appropriate visual display means for indication of the sensed dialysate solution electrolytic conductivity. Such monitoring of conductivity is desirable to insure that the dialysate solution has the proper level of salinity and electrolytic characteristics, so that vital components of the blood are not lost to the dialysate solution by ion diffusion across the mass transfer surfaces in the dialyzer.

From the conductivity sensing assembly 105, the dialysate solution is passed through the negative pressure regulator/flow controller assembly 107. This assembly has negative pressure adjustment means and negative pressure monitoring means disposed therein. As indicated in discussion earlier herein, negative pressure is employed on the dialysate solution side of the mass transfer member in the dialyzer means to effect water removal from the blood by ultrafiltration. The negative pressure of the dialysate solution may be adjusted in assembly 106 by adjustment means such as an elliptical flow valve or needle valve which serves to regulate negative pressure and control the flow rate of dialysate solution through the flow circuit.

Located downstream from the negative pressure regulator/flow controller assembly 106 is negative pressure monitoring means 107. The monitoring means may suitably comprise a negative pressure sensor which is operatively connected to visual display means for indicating the magnitude of the negative pressure of the dialysate solution. The negative pressure sensor may also be operatively connected with the negative pressure adjustment means in assembly 106, whereby negative pressure of the dialysate solution may be maintained at a predetermined level.

Dialysate solution discharged from the negative pressure sensor 107 is passed in line 108 to line 109 and from line 109 through the dialyzer means 112. In the dialyzer means, the dialysate solution is passed in indirect mass transfer dialyzing relationship with the waste impurity-containing blood flowing therethrough from the blood flow circuit comprising blood lines 119 and 121. As a result of such mass transfer in the dialyzer means 112, waste impurities from the blood are transferred to the dialysate solution and the resulting waste impurity-enriched dialysate solution is discharged from the dialyzer means 112 in line 113. From line 113, the dialysate solution passes in line 114 to blood leak detector assembly 115. This assembly comprises means for detecting blood leakage into the dialyzate solution flow stream together with means for converting the blood leakage detection into a transmittible signal. This signal is transmitted by suitable transmission means to blood leakage detection output means, which may suitably comprise visual display or audio alarm means. These blood leak detection means are provided to insure that only direct mass transfer—i.e., diffusional and osmotic transfer of species across the dialyzer mass transfer member—is occurring without direct cross-leakage between the respective fluids in the dialyzer means.

After flow through the blood leak detector assembly 115, the dialysate solution is pumped by peristaltic pump means 116, which functions to advance dialysate solution through the dialysate solution flow circuit, and the resulting pumped dialysate solution is discharged from the hemodialysis module "C" in line 117.

In the above-described dialysate solution flow circuit portion associated with hemodialysis module "C", there is provided a branch line 110 having bypass regulator means 111 associated therewith. The purpose of bypass regulator means 111 and branch line 110 is to divert dialysate solution from line 108 into line 114, so that the dialysate solution bypasses the dialyzer means 112. The bypass regulator means 111 is arranged and constructed such that dialysate solution is diverted through line 110 and bypasses the dialyzer means 112 when the dialysate solution lacks the proper characteristics for dialysis. To this end, the bypass regulator means 111 may be operatively coupled with one or more of the temperature sensing assembly 104, conductivity sensing assembly 105, negative pressure sensing assembly 107 and blood leak detection means 115, so that the dialysate solution goes into bypass flow when the dialysate solution sensed characteristics exceed allowable limits or when blood leakage is detected in the dialysate solution by the blood leak detector means 115.

Figure 2:
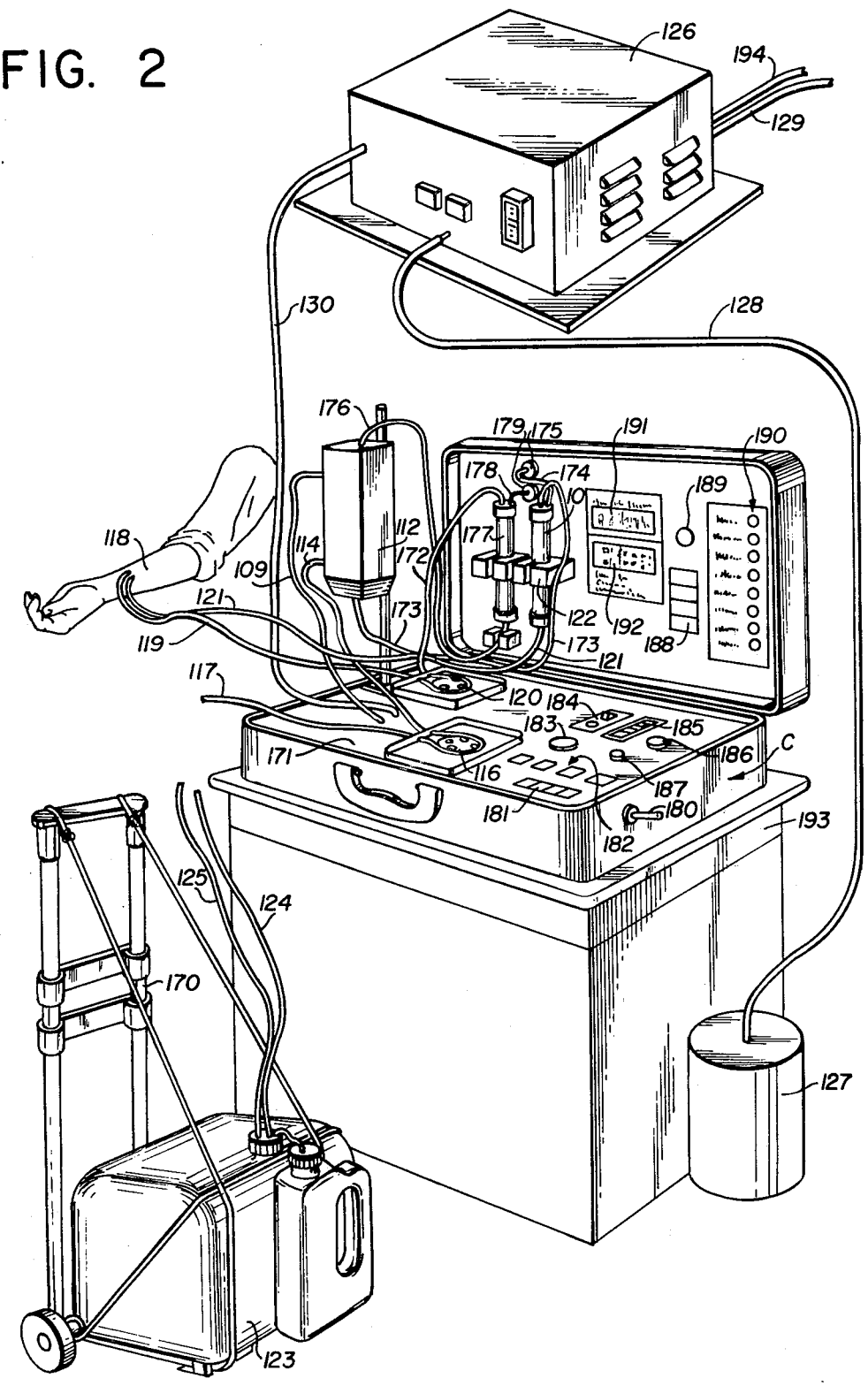
FIG. 2 is a perspective view of a hemodialysis system of a type corresponding to that shown in the schematic block diagram of FIG. 1.

FIG. 2 is a perspective view of a compact portable hemodialysis system of the general type shown in FIG. 1. Corresponding system elements have the same reference numerals in FIGS. 1 and 2.

Referring now to FIG. 2, the hemodialysis module "C" is contained in a unitary suitcase-type enclosure. The enclosure comprises upper and lower sections which are hingedly joined together and which, when the dialysis module is not in use, are fitted and retained together with the aid of suitable complimentary locking members (not shown). When so fitted together, the hemodialysis module enclosure is highly compact, and may for example measure 21 inches in length by 12 inches in width by 6 inches in height. In practice, the enclosure casing may be formed of light weight material such as aluminum so that the weight of the entire enclosure assembly is maintained sufficiently low for portability, as for example on the order of 25 pounds.

The hemodialysis module is designed to operate on conventional 120/220 volt alternating current, as provided to the module by the power line 180 entering the enclosure lower section. In the enclosure lower section, the power required for operation of the various monitoring and display means is provided by a direct current power supply located beneath the facing panel of the lower section.

As shown, the hemodialysis suitcase module "C" is disposed on a stand 193. The proportioning system 126 is positioned on an overlying shelf above the hemodialysis suitcase module and the dialysate concentrate container 127 is disposed on the floor beside stand 193. As associated with the hemodialysis system is the dialysate solution batch recirculation means including dialysate solution container 123 with feed inlet and return lines 124 and 125, respectively, joined thereto. Container 123 is positioned on the carrier means 170 for ease of portability.

The blood flow circuit for the FIG. 2 system comprises tubing segments 119, 172, 176, 173 and 121 which may be of a conventional type formed of transparent polyvinylchloride, polyurethane, or silicone elastomer. Waste impurity-containing blood is accessed from the patient as for example by an arterio-venous fistula and is passed in the aerterial feed line 119 to the peristaltic blood pump 120, which may suitably be of a type as disclosed and claimed in U.S. patent application Ser. No. 720,672 filed Sept. 7, 1976 in the name of J. T. Hutchisson, incorporated herein to the extent pertinent. Peristaltically pumped blood from the blood pump 120 is passed in line 172 to the arterial drip chamber 177. Arterial drip chamber pressure is measured by means of the pressure monitor line connector 178, which connects the drip chamber 177 with a pressure monitor means 179. From the arterial drip chamber, the blood passes in line 176 through the dialyzer 112. The dialyzer 112 may suitably be of the parallel flow hollow fiber type previously described having for example about 1.50 meters$^2$ of membrane mass transfer exchange area for dialysis. In the dialyzer, the waste impurity constituents of the blood such as urea, uric acid and creatinine diffuse from the blood across the membrane into the dialysate solution. Water removal from the blood is carried out by ultrafiltration effected by using up to 350 mm Hg negative pressure on the dialysate solution side of the membrane and up to 500 mm Hg overall transmembrane differential pressure. Typically, 1 to 2 liters of water is removed during the dialysis treatment.

From the dialyzer 112, which is supportively positioned at the side of the enclosure unit by means of a clamp and stand assembly joined to the side wall of the enclosure lower section, the waste impurity-depleted blood is flowed in line 173 to the venous drip chamber having air leak detection means 122 associated therewith, the latter serving to detect the presence of gas bubbles in the blood flowing through the venous drip chamber. Pressure monitor line connector 174 is joined to the venous drip chamber and communicates with the venous pressure monitoring means 175 which monitors pressure in the venous drip chamber. From the venous drip chamber, the waste impurity-depleted blood is returned to the patient in line 121.

The dialysate solution flow circuit for the FIG. 2 system may be open loop (i.e., single-phase flow) or closed loop, depending on whether the batch recirculation container 123 or the proportioning system 126 is used as a source of dialysate solution for the hemodialysis module. In FIG. 2, the proportioning system 126 is shown as being operatively connected with the hemodialysis module "C", so that the hemodialysis system is adapted for open loop, single-pass flow of dialysate solution. In the open loop arrangement as shown, the dialysate solution flow circuit comprises tubing segments 130, 109, 114 and 117, which also may be of a conventional type as formed of polyvinylchloride, polyurethane or silicone rubber.

The proportioning system 126 for the open loop dialysate solution flow circuit, as described in greater detail hereinafter, is provided in a unitary enclosure as shown. The proportioning system is designed to operate on conventional 120/220 volt alternating current, as provided to the proportioning system by the power line 194 entering the enclosure at the rear portion thereof. Water is provided for the proportioning system 126 in line 129 which may suitably be coupled with water source means, as for example a household water faucet. Dialysate concentrate is provided to the proportioning system from container 127 and flows therefrom through line 128 to the proportioning system 126 for mixing therein in a predetermined ratio with the water from line 194 to form dialysate solution for hemodialysis. Dialysate solution is discharged from the proportioning system 126 in line 130. From line 130 the dialysate solution passes through various sensing and control means as described previously in connection with the FIG. 1 block diagram and as associated in the FIG. 2 system with the detachable dialysate solution manifold 171. The dialysate solution manifold assembly may suitably be constructed in a manner generally similar to that shown and described in U.S. patent application Ser. No. 720,673, now U.S. Pat. No. 4,079,007, filed Sept. 7, 1976 in the name of J. T. Hutchisson. After passage of the dialysate solution through the various sensing and control means associated with the dialysate manifold 171, the dialysate solution is passed in line 109 to the dialyzer 112 for mass transfer of waste impurities from the blood to the dialysate solution. Waste impurity-enriched dialysate solution is discharged from the dialyzer 112 in line 114 and passed to the peristaltic dialysate solution pump 116, as described hereinafter in greater detail. The dialysate solution is advanced through the dialysate solution flow circuit by the peristalic pump 116 and dialysate solution from the pump is discharged from the system in line 117. As described earlier, line 117 may suitably be coupled with drain or other waste disposal means for the impurity-enriched dialysate solution.

In the closed loop dialysate solution batch recirculation mode of operation, wherein the proportioning system 126 is not employed, dialysate solution from container 123 is withdrawn therefrom in line 124 and passed from line 124 into the dialysate manifold assembly 171, in place of the previously described dialysate solution inlet line 130 associated with the proportioning system 126. For return of the dialysate solution from the dialysate solution flow circuit to the container 123, discharge line 117 from the dialysate solution pump 116 is joined as by suitable connection means (not shown) to the return line 125 which in turn is joined to the dialysate solution container 123. In this manner, dialysate solution from container 123 is withdrawn in line 124 and flowed through the dialysate solution flow circuit associated with the hemodialysis module "C" in the same manner as previously described in connection with the use of the proportioning system 126, but with the impurity-enriched dialysate solution being returned from discharge line 117 through return line 125 to the dialysate solution container 123.

On the facing panel of the upper section of the suitcase enclosure, a series of safety control lights 190 are provided to indicate the condition of the system at any given time. The uppermost light in the series is green in color and is illuminated when all constituents of the hemodialysis system are functioning within allowable limits. The remaining lights in the series are red in color. The lowermost light in the series is illuminated when the hemodialysis module dialysate solution flow circuit operates in the by-pass mode, as described earlier herein in connection with FIG. 1, due to one or more of the monitored characteristics of the dialysate solution exceeding allowable operating limits. The remaining lights are warning lights which are illuminated when a monitored characteristic of the dialysate solution exceeds allowable limits; controlled lights are sequentially provided for dialysate solution temperature, dialysate solution conductivity, venous pressure as monitored by pressure monitoring means 175, arterial pressure as monitored by pressure monitor means 179, dialysate solution negative pressure, blood leakage into the dialysate solution and air leakage or presence of gas bubbles in the blood flow circuit. The monitoring means in the hemodialysis module are also operatively arranged to actuate the audio alarm means 189 when one or more of the monitored parameters exceeds allowable operating limits.

Also located on the facing panel of the upper section of the suitcase enclosure is an array of switches 188. The uppermost switch is an audio alarm override, which, when the associated panel button is depressed, silences the audio alarm means 189. The next switch is an alarm override, which when depressed overrides the blood leak and air leak alarm set points. The next switch is appropriately illuminated to indicate normal operational functioning of the hemodialysis system. The lowermost switch has two settings which control the set point temperature for dialysate solution heating. The two positions of this switch correspond to dialysate solution temperature set points of 98° and of 100° which control the heating rate of the dialysate solution by the heating means in the dialysate manifold to control the dialysate solution temperature at the selected level. Under normal operating conditions, the 98° F. position of the switch is selected; under low ambient temperature conditions, the 100° F. set point is selected to maintain blood passing in indirect heat exchange relationship with the dialysate solution in the dialyzer at approximately normal body temperature.

Located adjacent to the audio alarm 189 and safety control switches 188 on the facing panel of the upper section of the suitcase enclosure are numerical display means 191 and 192. The upper numerical display 191 provides a continuous numerical display of the venous pressure as monitored by the venous pressure monitor 175. The lower display 192 is coupled with the respective sensing means for dialysate solution temperature, dialysate solution conductivity, dialysate solution negative pressure and blood arterial pressure, and the particular parameter displayed is selected by the display switches 181 located on the facing panel of the lower section of the suitcase enclosure. In the array of switches 181 are individual switches for selecting each of the aforementioned display parameters, so that depression of the appropriate button associated with the switch means 181 initiates the transmission of a signal from the sensing means associated with the specific parameter to the visual display 192, so that instantaneous numeric values of the monitored parameter are displayed on display 192.

Located directly above the array of display switches 181 is a group of four switches 182. These switches include a switch for actuating the dialysate solution pump 116, a switch for relaxing the set point limits of the monitored parameters, as used to avoid actuation of the various audio and visual alarms during start-up of the hemodialysis system, a switch which when depressed sets the set points of the various monitored and controlled operating parameters for normal dialysis operation and a switch which deactivates the various monitoring and control means, as employed during rinse cleaning of the system.

Located above the aforementioned arrays of switches on the facing panel of the lower section of the suitcase enclosure are a blood pump speed control adjustment means 183 which is coupled with variable motor speed control means by which drive means are coupled with the blood pump head assembly 120 for rotation thereof at a speed as for example in the range of from 50 to 400 rpm, a power fuse 187, a conductivity sensor calibration control 184 which is employed to adjust the conductivity reading on numerical display 192 for calibration of the conductivity monitoring system with reference to a solution of known electrolytic conductivity, an AC voltage meter 185 which indicates the amount of line voltage received by the hemodialysis module from power line 180 and a blood leak detector sensitivity calibration means 186 which may be used to adjust the detection level at which the blood leak detector senses the presence of blood in the dialysate solution flowing through the dialysate solution flow circuit portion downstream from dialyzer 112.

Figure 3:
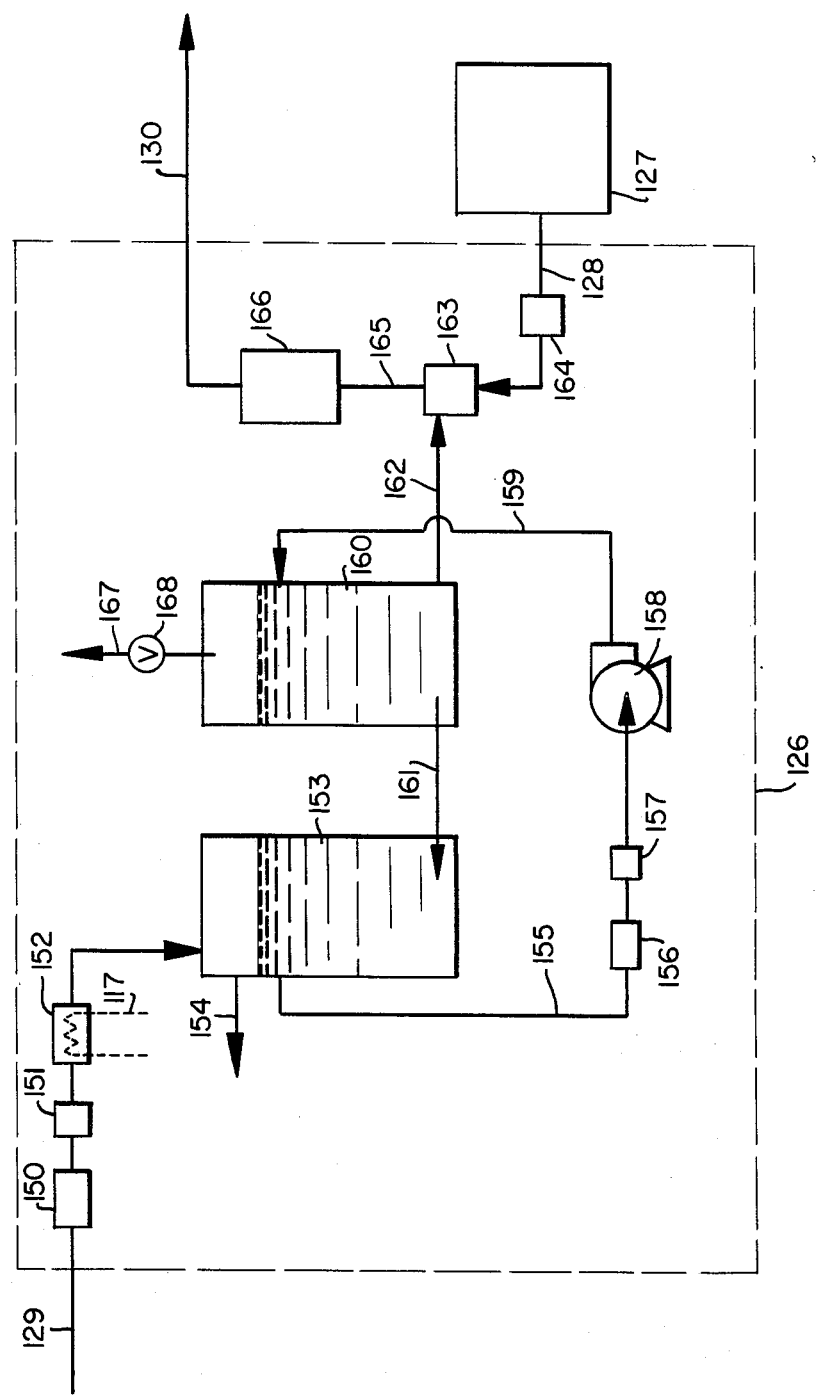
FIG. 3 is a schematic diagram of a proportioning system suitable for use in the FIGS. 1 and 2 systems.

FIG. 3 is a schematic block diagram of a proportioning system 126 of a type suitable for use in the FIGS. 1-2 hemodialysis system. Water from suitable source means such as a household faucet tap is introduced to the proportioning system 126 in line 129. Prior to introduction of the water to the proportioning system, the water may be subjected to filtration, deionization or reverse osmosis for removal of undesirable constituents from the water (means not shown). Suitable means for carrying out the aforementioned water treatment steps are well known to those skilled in the art and form no part of the present invention.

Water flowing into the proportioning system 126 in line 129 first passes through the pressure shut-off switch 150, which is adapted to shut off the flow of water through line 129 if water pressure exceeds a predetermined upper level or decreases below a predetermined lower level. The pressure shut-off switch is of conventional type; suitable set point upper and lower limits for the pressure switch are 100 psig and 19 psig, respectively. Such pressure shut-off set point limits are employed to avoid the possibility of damage to system components due to either excessive pressure on the one hand or inadequate pressure on the other.

From the pressure shut-off switch 150, the water in line 129 passes through the flow controller 151, which functions to maintain a constant flow rate of water in line 129. The flow controller may suitably be of a type which is designed to maintain a constant pressure differential across an integral manual flow regulating valve. In this flow controller, an internal diaphragm-actuated control valve is positioned by the force exerted by the influent liquid pressure on one side of the diaphragm, as opposed by the outlet liquid pressure and valve bias (spring) means on the other side of the diaphragm. In this manner, variations in the upstream or downstream pressure levels disturb the balance of forces on the diaphragm, thereby causing the control valve to open or close as necessary to maintain a fixed pressure differential across the manual flow regulating valve. In operation, the manual flow regulating valve is set to deliver a flow rate of 500-600 ml/min in line 129. A suitable flow controller for this purpose is the Brooks Model Series 8800 manufactured by Brooks Instrument Division of Emerson Electric Company, Hatfield, Pennsylvania.

The water in line 129 next passes to the heater 152, wherein the temperature of the water is raised to approximately 90° F. The heater may be of any suitable conventional type for this purpose. As discussed earlier herein, the dialysate solution which is passed through the dialyzer must be at approximately normal body temperature (98.6° F.), in order to preclude undue heating or cooling of the blood by heat transfer in the dialyzer. Accordingly, the water in line 129 is heated to a level which approaches but is somewhat lower than the temperature finally desired for the dialysate solution which is formed by admixture of water and dialysate concentrate. In this manner, the dialysate solution discharged from the proportioning system requires only a low level of further heating in the dialysis module "C" of FIGS. 1-2. For this reason, i.e., the low level of further heating required, the dialysate solution heating means in the hemodialysis module "C" can be relatively small in size, as is desired for compactness and portability of the hemodialysis module suitcase enclosure shown in FIG. 2. In order to minimize the heating requirements for the heater 152, this heating means may suitably comprise a heat exchanger for passing water from line 129 in indirect heat exchange relationship with waste dialysate solution discharged from the dialyzer, flowing through the heat exchanger in line 117, for recovery of heat from the waste dialysate solution. Such heat exchanger arrangement minimizes the net heat input necessary to raise the temperature of the influent water to the desired level and thus allows the use of a relatively small heater device for the proportioning system.

The water entering the proportioning system in line 129 characteristically contains entrained and dissolved gases, such as may result for example from aeration and entrainment of gas in water supply pipes and faucet fittings. Inasmuch as the temperature of the water in line 129 is substantially elevated, as for example from a temperature of about 35° F. to about 90° F., gases which were dissolved in the water entering line 129 desolubilize from the elevated temperature water discharged from heater 152, as a result of the fact that gas solubility in liquids is generally a decreasing function of temperature. As a result, the water at elevated temperature discharged from the heating means 152 contains a significant component of desolubilized gases.

In general the presence of gas in the dialysate solution passed to the dialyzer is severely detrimental to the safety and efficacy of the hemodialysis treatment. Accordingly, the proportioning system 126 is provided with deaeration means for removing soluble gases from the heated water prior to passage thereof to the proportioning means. From heater 152, heated water containing desolubilized gases is discharged into line 129 at a flow rate of for example 550 ml/min, a temperature of 85°–95° F. and a pressure of 19–100 psig, and passed to the first reservoir tank 153. The first reservoir tank 153 has a volume of from 150–400 ml and may suitably comprise a cylindrical vessel having a diameter of 2 inches and a height of 7 inches. The first reservoir tank 153 is provided with venting means such as vent conduit 154 to permit gases desolubilized from the water in the heating in heater 152 to disengage from the heated water to form partially deaerated water. In addition to serving as an outlet for gas desolubilized from the water, vent conduit 154 also functions as an overflow discharge means for maintaining liquid level in the first reservoir tank below a predetermined level. For this purpose, the vent conduit 154 may be positioned for example 5¼ inches above the floor of the 7 inch tall first reservoir tank. In connection with its function as an overflow discharge means, the vent conduit 154 may be equipped with a siphon breaker (not shown) to prevent back-up of the wasted water into the first reservoir tank 153.

In operation, flow controller 151 is adjusted to provide a volumetric water flow rate of 10–20% in excess of that required in the dialysate solution flow circuit of the hemodialysis system. For example, the flow controller 151 may be adjusted to regulate the flow water in line 129 at a level on the order of 550 ml/min, so that excess liquid at a flow rate of up to 40 ml/min is discharged via the overflow discharge vent conduit 154. The purpose of providing a small excess of heated water to the first reservoir tank 153 is to insure that the water supply in the first reservoir tank is not depleted in operation. Without excess flow introduction, the flow rate of heated water into the first reservoir tank would have to match the flow of water in the dialysate solution being pumped from the proportioning system by the pumping means in the dialysate solution flow circuit, a match which is difficult to achieve continuously in practice. By providing overflow discharge means for maintaining liquid level in the first reservoir below a predetermined level and introducing a 10–20% excess flow of liquid into the first reservoir tank 153, the excess flow rate allows for a corresponding 10–20% fluctuation in the flow rate of dialysate solution discharged from the pumping means in the dialysate solution flow circuit. In this manner, variations in dialysate solution flow rate from the pump in the dialysate solution flow circuit are accommodated by a correspondingly varied influent water supply for make-up of dialysate solution. Nonetheless, in some applications of the present invention, variations in flow rate in the dialysate solution flow circuit of the hemodialysis system may be tolerable, so that excess liquid flow into the first reservoir tank 153 and the use of vent conduit 154 as an overflow discharge means for maintaining liquid level in the first reservoir tank below a predetermined level may not be necessary.

Partially deaerated water from first reservoir tank 153 is removed therefrom in conduit 155. This conduit has an adjustable flow restriction means 156 disposed therein for reduction in pressure of the partially deaerated water passed through the conduit to further desolubilize gases therefrom and to form lower pressure water with desolubilized gas dispersed therein. A suitable flow restriction means for this purpose is the Neutrol needle valve, ⅛ inch size, EFL 10B, manufactured by Deltrol Corporation, Bellwood, Illinois. The flow restriction means is adjusted to provide an appreciable pressure drop in the liquid, as for example to 600–750 mm Hg pressure in the liquid discharged from the flow restriction means while allowing a flow rate of water through line 155 of 600–750 ml/min. The purpose of the adjustable flow restriction means 156 is to reduce the pressure of the liquid flowing in line 155 to below the atmospheric pressure level of the partially deaerated water withdrawn from first reservoir tank 153, so as to depressurize the liquid and release additional soluble gases therefrom. Downstream from adjustable flow restriction means 156 is a vacuum monitoring means 157 which may suitably comprise a conventional vacuum gage. Such monitoring means permit the liquid pressure level of the water discharged from the adjustable flow restriction means to be readily determined, so that any necessary adjustment of flow restriction means 156 can readily be made to maintain a predetermined pressure level in the water discharged therefrom.

The terminal end of conduit 155 is joined to an inlet of a vacuum pump 158. As used herein, the term vacuum pump refers to a positive displacement pump, adapted to operate in a vacuum mode, that is, to receive liquid at pressures below normal atmospheric pressure for pumping thereof to higher pressure. Pump 158 is preferably of a type which is magnetically coupled and thus leak-proof and free of contamination of the water being pumped. A suitable pump is the Model 12-50-316 gear pump, manufactured by Micropump, Incorporated, Concord, California. As mentioned, pump 158 is operated in the vacuum mode and pumps 600–750 ml water/min at a pressure of for example 740 mm Hg. negative pressure in the liquid entering the pump inlet. From an inlet pressure of 600–750 mm Hg, the liquid in pump 158 is pressurized to approximately normal atmospheric pressure level. A conduit 159 is joined at one end to an outlet of the vacuum pump 158 for discharging higher pressure water with desolubilized gas dispersed therein from the pump. A second reservoir tank 160 is joined to the other end of the conduit 159 for receiving discharged higher pressure water therefrom. The second reservoir tank is provided with venting means to permit the desolubilized gas to disengage from the higher pressure water therein to form finally deaerated water. The venting means may suitably comprise a vent conduit 167 from the reservoir having a manually closable vent valve 168 therein.

The second reservoir tank 160 may be of the same size and dimensions as the first reservoir tank 153, so that for example the second reservoir may comprise a cylindrical vessel 2 inches in diameter and 7 inches in height. Although the first reservoir tank 153 and second reservoir tank may be provided as separate tanks as shown, it is also contemplated that the respective reservoirs may be fabricated concentrically with respect to one another, with a smaller second reservoir tank disposed within a larger first reservoir tank. In this concentric arrangement, the volume of the interior second reservoir tank would be equal to the annular volume between the adjacent walls of the first and second reservoir tanks. Such concentric arrangement may be desirable for reasons of achieving small size and compactness of the overall proportioning system 126. From second reservoir tank 160, finally deaerated water is transferred in line 162 to the downstream proportioning means.

In order to enhance removal of soluble gases by the above-described aeration means, a conduit 161 is provided, joining the first reservoir tank 150 with the second reservoir tank 160 for recirculation of a portion of the finally deaerated water from the second reservoir tank to the first reservoir tank. Such recirculation conduit is not an essential feature of the deaeration system, but is desirably employed in practice to enhance removable of soluble gases in the deaeration system. With the previously described illustrative water flow rate of 600-750 ml/min in conduit 155, and hence in conduit 159 discharging into the second reservoir tank 160, approximately 20-50% of the water entering the second reservoir tank 160 from line 159 is recirculated in conduit 161 to the first reservoir tank 153, so that the flow rate of finally deaerated water discharged from the second reservoir tank 160 in line 162 is suitably on the order of 510 ml/min. Since, when recirculation conduit 161 is employed, the flow rate of water in line 159 is adjusted to be greater than the flow rate of finally deaerated water discharged in conduit 162, the direction of flow through conduit 161 is always from the second reservoir tank 160 to the first reservoir tank 153. As mentioned, approximately 20-50% of the water entering the second reservoir tank 160 in line 159 is recirculated in conduit 161 to the first reservoir tank 153, from which the recirculated liquid undergoes further deaeration by flow through line 155, having adjustable flow restriction means 156 disposed therein, pump 158 and conduit 159 for return to the vented second reservoir tank 160.

While both the first reservoir tank 153 and the second reservoir tank 160 are vented to the atmosphere, the second reservoir tank 160 is equipped with a closable vent, such as manually closable vent valve 168 disposed in vent conduit 167. The provision of closable vent means is desirable inasmuch as it allows drainage of the first and second reservoir tanks when the proportioning system is taken out of service. Drainage is carried out by emptying the contents of the second reservoir tank 160 and then the first reservoir tank 153 in sequence. To carry out the drainage operation, the manually closable vent valve 168 in vent conduit 167 from the second reservoir tank 160 is closed and the flow of influent water to the proportioning system in line 129 is shut off along with the vacuum pump 158, while the dialysate solution pump means in the dialysate solution flow circuit of the hemodialysis module is maintained in operation. By the action of the pump means in the downstream portion of the dialysate solution flow circuit, the liquid content of second reservoir tank 160 is drawn out through discharge conduit 162. As the second reservoir tank is evacuated, the liquid remaining in the first reservoir tank is drawn into the second reservoir tank via the connecting conduit 161, in response to the pressure differential between the respective reservoir tanks.

From second reservoir tank 160, conduit 162 transfers the finally deaerated water to the proportioning means comprising mixing valve 163. In the mixing valve 163, the finally deaerated water is mixed with dialysate concentrate in a predetermined ratio to form dialysate solution for hemodialysis. Dialysate concentrate is supplied to the mixing valve from dialysate concentrate container 127, from which dialysate concentrate is removed in conduit 128 by the action of a pump 164 disposed therein and passed to the mixing valve 163. After the water and dialysate concentrate are mixed together in the mixing valve 163, the resulting dislysate solution is discharged from the mixing valve in conduit 165 and passed to the conductivity monitoring means 166. The conductivity monitoring means 166 may be associated with visual display means indicating the measured electrolytic conductivity of the dialysate solution so that a patient or user of the system can readily detect fluctuations in the value of electrolytic conductivity of the dialysate solution from the desired value and correspondingly adjust the speed of dialysate concentrate pump 164 to alter the relative proportions of water and dialysate concentrate being mixed together, so as to adjust the value of electrolytic conductivity of the dialysate solution discharged from the mixing valve to the desired value. Alternatively, the conductivity monitoring means 166 may be coupled to the dialysate concentrate pump 164 as for example by a feedback circuit which functions to adjust the speed of pump 164 to vary the relative proportions of finally deaerated water and dialysate concentrate being mixed, in response to a sensed deviation from a set point value of electrolytic conductivity, so as to maintain electrolytic conductivity at a predetermined value. The mixing ratio of finally deaerated water and dialysate concentrate in mixing valve 163 may suitably be in a volumetric ratio of approximately 34:1, corresponding for example to a flow rate of finally deaerated water in conduit 162 of 510 ml/min and a flow rate of dialysate concentrate in line 128 to the mixing valve of 15 ml/min, to form dialysate solution discharged in line 165 from the mixing valve 163, at a flow rate of 525 ml/min, a temperature of 85-95° F. and a pressure of approximately normal atmospheric pressure. From the conductivity monitoring means 166, the dialysate solution is discharged from the proportioning system in line 130 and passed through the hemodialysis solution flow circuit in the hemodialysis module, in the previously described manner. One advantage of the proportioning system as described above is that it provides dialysate solution for the hemodialysis system at substantially the same conditions, i.e., pressure, temperature and conductivity, as dialysate solution provided to the hemodialysis system from a batch supply container. Such substantial identity of dialysate solutions from the respective source means allows the hemodialysis module to be quickly and easily switched from one source means to the other—from the batch supply container to the proportioning system and vice versa—without alternation of the apparatus or operating conditions in the hemodialysis module.

Figure 4:
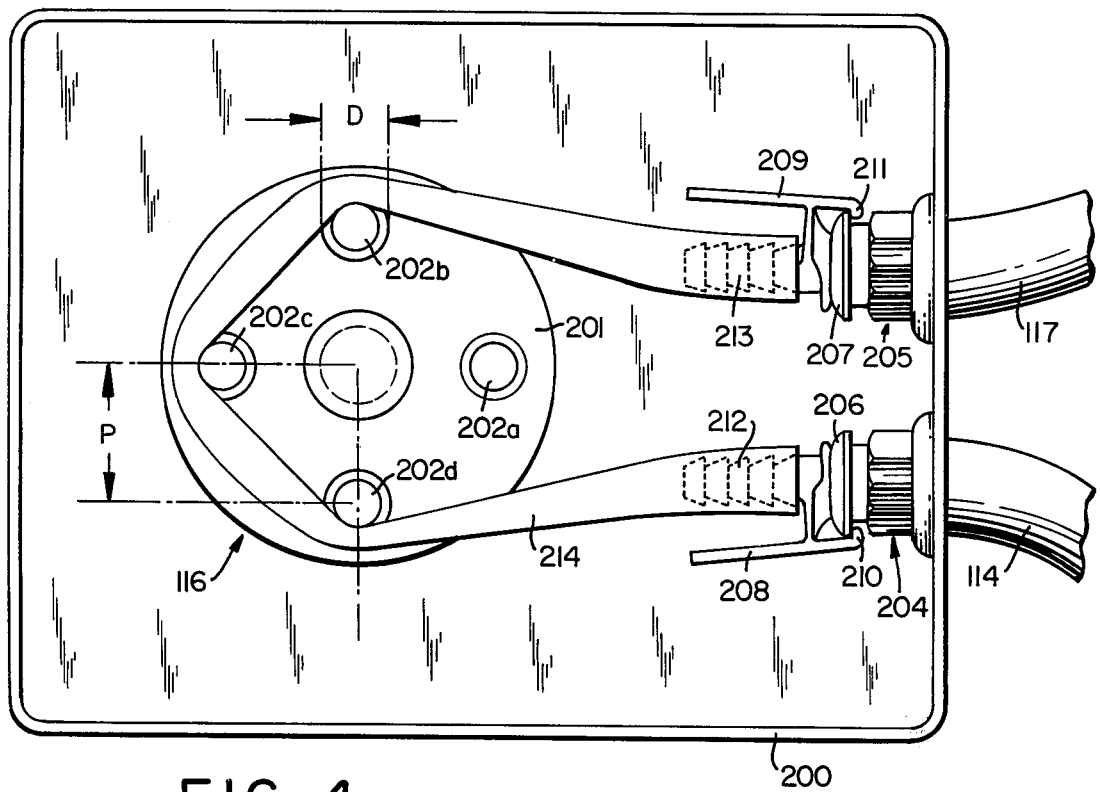
FIG. 4 is a plan view of a dialysate solution pump according to the present invention as suitably employed in the FIG. 2 hemodialysis system.

FIG. 4 is a plan view of the peristaltic dialysate solution pump assembly employed in the FIG. 2 hemodialysis system, showing the dimensional characteristics thereof. As shown, the pump 116 is disposed in the rectangular dish-like enclosure member 200. Pump 116 comprises a pump head assembly as illustrated which includes the pump head base member 201. The pump head base member 201 has a raised cylindrical spindle portion 203 which is adapted to fit over a rotatable shaft coupled with motor drive means for the pump assembly. In this manner, the pump head base member 201 is position for rotation about a fixed axis. Mounted on the pump head base member 201 by suitable bolt or screw fastener means for the basis member fixed axis are four circumferentially spaced-apart rollers 202a-d.

The dialysate solution flow circuit portion associated with the dialysate solution pump comprises tubular segments 114 and 117 which pass through an end wall of the enclosure 200 and terminate at fittings 204 and 205 respectively, the fittings being suitably attached to the enclosure end wall. The fittings 204 and 205 comprise flanged female connectors 206 and 207, respectively. Engaging the respective female connectors are male connectors 208 and 209. The male connectors are held in position by means of inwardly directed finger members 210 and 211 which lock around the flange portions of the respective female connectors 206 and 207, so that the male connectors may be quickly disconnected from the female connectors by pressure on the respective finger members of the male connectors so as to disengage the inwardly extending finger portions from the flange portions of the respective female connectors. The male connectors are provided with barbed projections 212 and 213 to which are joined the respective ends of a flexible resilient tubing pumping section 214 through which dialysate solution is pumped. The connectors and associated fittings described above function as means for anchoring the end segments of the flexible resilient tubing pumping section 214 such that the tubing is tensionally extended around the pump head assembly, being simultaneously engaged and compressed by at least two of the circumferentially spaced-apart rollers, the rollers being mounted for longitudinal movement of the points of compression along the tubing during rotation of the pump head assembly to advance dialysate solution through the tubing.

The dialysate solution pump shown in FIG. 4 represents an improvement which has unexpectedly been discovered for providing a substantially constant flow rate in the dialysate solution flow circuit of the hemodialysis system, despite variations in negative pressure which are imposed on the dialysate solution in the flow circuit to accommodate the ultrafiltration requirements of the patient being treated. As a result, dialyzing efficiency is substantially increased, with the dialysate solution pump maintaining uniform flow in the dialysate solution flow circuit even at high negative pressure levels, so that the dialysis treatment can be carried out within a relatively short period of time even at high negative pressure levels.

Under the improvement, the peristaltic dialysate solution pump means comprises four rollers mounted on the base member, each roller having a maximum diameter D, as shown in FIG. 4, of between 0.25 and 0.75 inch and circumferentially spaced apart at an angle of 90° from the other rollers with a radial distance P between the roller axis and the pump head assembly base member 201 fixed axis of from 0.50 to 1.50 inches. The improvement also requires a flexible resilient tubing pumping section having a length, as measured longitudinally along the tubing between the anchored end segments thereof, of from 6.75 to 11.0 inches, a wall thickness of from 0.07 to 0.125 inch, and an internal diameter of from 0.18 to 0.35 inch, with drive means coupled to the pump head assembly for rotation thereof at a speed in the range of from 150 to 400 rpm.

Although peristaltic pump means have been employed by the prior art for pumping dialysate solution in hemodialysis system dialysate solution flow circuits, the prior art has not been able to achieve substantial uniformity of flow rate from the pump under conditions of varying dialysate solution negative pressure. The pump of this invention represents a striking improvement over the peristaltic pump disclosed in U.S. patent application Ser. No. 720,672 filed Sept. 7, 1976 in the name of J. T. Hutchisson, as will be shown hereafter in greater detail.

The peristaltic pump disclosed in the aforementioned U.S. Ser. No. 720,672 as suitable for pumping dialysate solution in the hemodialysis system dialysate solution flow circuit, comprises three rollers mounted on a base member, each roller having a diameter of between 0.25 and 0.75 inch and circumferentially spaced apart at an angle of 120° from the other rollers with a radial distance between the roller axis and pump head assembly base member fixed axis of from 0.50 to 1.25 inches. This prior art pump employs a flexible resilient tubing pumping section having a length, as measured longitudinally along the tubing between the anchored end segments thereof, of from 6.0 to 6.75 inches, a wall thickness of from 0.03 to 0.10 inch and an internal diameter of from 0.18 to 0.25 inch, with drive means connected to the pump head assembly for rotation thereof at a speed in the range of from 200 to 600 rpm.

Although the pump of this invention is structually similar to the prior art pump of U.S. Ser. No. 720,672 in many respects, the pump of this invention embodies several critical structural differences from such prior art pump, which permit a striking improvement in uniformity of dialysate solution flow rate with variation in dialysate solution negative pressure to be achieved. These critical structural differences of the peristaltic pump of this invention relative to the prior art pump of U.S. Ser. No. 720,672 include the provision of a greater number of rollers, with the rollers having a generally convex surface profile as opposed to the flat surface profile taught by the prior art, and the provision of a generally longer length flexible resilient tubing pumping section.

In order to understand fully the advance achieved by the peristaltic pumping means of this invention, it is first necessary to consider the effects of varying negative pressure dialysate solution on the output flow rate of dialysate solution from a prior art peristaltic pump incorporated in the dialysate solution flow circuit. In the dialysate solution flow circuit, a pumping section of flexible resilient tubing in the dialysate solution flow circuit is tensionally extended around the peristaltic pump head assembly, being simultaneously engaged and compressed by at least two circumferentially spaced-apart rollers. The rolles are mounted for longitudinal movement of the points of compression along the tubing during rotation of the pump head assembly to advance dialysate solution through the tubing. At the points of contact of the tubing pumping section with the pump head rollers, the rollers compress the tubing and alter its cross-section from the tubing's uncompressed normal circular cross-section. The extent of reduction of cross-sectional area of the tubing at the point of contact with a roller is commonly characterized as the degree of occlusion of the flexible resilient tubing pumping section.

In general the pumping efficiency of a peristaltic pump is a function of the degree of occlusion for the tubing and the volume of liquid in the segment of tubing between adjacent roller compression points. The volume of liquid in the tubing segment between adjacent roller compression points is a function of the local cross-sectional area of the tubing along its length between the adjacent compression points, which is dependent on the degree of occlusion and the length of the tubing between adjacent compression points. The local cross-sectional area of the tubing segment between adjacent rollers is dependent on the degree of occlusion at the roller compression points, inasmuch as roller compression at the point of contact tends to flatten out the tubing segment and this flattening effect is exerted on the tubing for some distance away from the roller. The pumping efficiency of the peristaltic pump is even more directly influenced by the degree of occlusion of the tubing section by virtue of the fact that any less-than-total occlusion of the tubing permits back flow of liquid from the tubing section portion downstream of the roller to the tubing section portion upstream of the roller, through the unoccluded cross-section of tubing at the point of compression. For this reason, the prior art pump disclosed in U.S. patent application Ser. No. 720,672, when employed for the pumping of dialysate solution, has employed a relatively short length of tubing pumping section to provide high tension in the tubing section extended around the pump head assembly, so as to obtain complete occlusion, i.e., total closure, of the tubing at the points of contact with the roller members. Such total occlusion at the points of compression of the tubing with the rollers has been employed to maximize pumping efficiency, through the prevention of back flow from the tubing section portion downstream of the roller to the tubing section portion downstream of the roller, thereby obtaining substantially complete positive displacement of the liquid contained in the tubing segment between adjacent rollers.

Despite total occlusion of the tubing sections at the points of roller contact in the prior art pump of U.S. patent application Ser. No. 720,672, which would presumptively provide high pumping efficiency, it has been found that the output flow rate of dialysate solution provided by this prior art pump decreases drastically with increasing negative pressure. Such flow rate—negative pressure characteristic represents a severe operating disadvantage for the prior art pump when employed to pump dialysate solution in the hemodialysis system, for the reason that it is generally desirable to vary the level of negative pressure of the dialysate solution being pumped through the dialyzer for dialysis treatment from patient to patient and, for a given patient, from run to run. The purpose of varying the dialysate solution negative pressure for dialysis from patient to patient or from run to run is to adjust the pressure gradient driving force, for mass transfer of water from the blood through the dialyzer mass transfer surface to the dialysate solution passed in indirect mass transfer dialyzing relationship with the blood, to the proper level so as to insure substantially complete removal of water from the blood during the dialysis treatment. In this regard the above-described prior art pump responds to increasing negative pressure with drastically reduced output flow of dialysate solution from the pump. The resulting reduction in dialysate solution flow rate in the dialysate solution flow circuit of the hemodialysis system adversely affects the overall efficiency of the dialysis treatment and requires significantly increased treatment time to effect the required removal of impurities from the blood being treated.

The reason for the above-described drastic reduction in dialysate solution output flow rate with increasing dialysate solution negative pressure in the prior art pump is associated with the employing of total occlusion of the tubing pumping section at the point of contact with the rollers which, ironically, is employed to enhance pumping efficiency. As discussed hereinabove, the tensioning of the tubing pumping section around the rollers of the pump head assembly of a peristaltic pump results in a flattening of the tubing cross-section extending along the length of the tubing section away from the point of compression of the tubing against the roller. The longitudinal extent of such flattening along the tube is a function of the degree of occlusion, with the degree of flattening and the longitudinal extent of the flattening effect along the tubing segment being greatest when the tubing section is fully occluded at the point of contact with the roller. In such a fully occuluded pump system, as an increased negative pressure is imposed on the liquid entering the tubing pumping section, the atmospheric pressure force acting on the external surface of the tubing section becomes correspondingly greater than the pressure force acting on the internal surface of the tubing section by the liquid flowing therethrough. This pressure differential tends to collapse the tubing from the configuration that it would otherwise assume if there were no such pressure differential. The tubing section in the totally occuluded pump system is particularly susceptible to further collapse by virtue of the fact that a significant portion of the length of the tubing pumping section is already flattened to a greater extent as a consequence of the total occlusion of the tubing at the points of contact with the rollers, as discussed above. In other words, the deformation of the tubing section due to the negative pressure differential is greater in a tubing section which is already flattened to some extent than in a tubing segment having an undeformed, normal circular cross-section. For this reason, the tubing section segments between adjacent rollers in the totally occuluded pump system tend to become highly collapsed with increases in dialysate solution negative pressure. This collapse of the tubing section portions between adjacent rollers substantially reduces the liquid volume contained in such tubing segments, so that the amount of dialysate solution which is advanced through the tubing by the pump is correspondingly reduced. For this reason, the totally occuluded prior art dialysate solution pumping system exhibits a drastic reduction in dialysate solution flow rate from the pump with increasing levels of dialysate solution negative pressure.

In view of the above-described deficiency of the prior art pumping system, it might be supposed that the use of relatively thick-walled tubing would mitigate the problem of the low flow rate at high negative pressure levels, since a relatively thicker walled tubing segment would be less susceptible to distortion by pressure differentials resulting from dialysate solution negative pressure. Despite this apparent advantage, however, relatively thick-walled tubing is not suitable for use in the pumping system, inasmuch as it is correspondingly more difficult to occlude properly for effective pumping. In this regard, it to be pointed out that there must be at least partial occlusion of the tubing segment at the points of compression with the rollers or else the pumping system will not function to advance dialysate solution through the tubing. Furthermore, the approach of the prior art has been to occlude totally the tubing section at the points of compression with the rollers, which would be correspondingly more difficult than mere partial occlusion. For such a reason, the use of tubing wall thicknesses substantially greater than the level employed by the prior art pump, e.g. substantially greater than 0.10 inch, does not provide a viable solution to the foregoing problem.

Relative to the peristaltic pump means of the prior art, the dialysate solution pump of this invention provides the unexpected improvement of a substantially constant output flow rate of dialysate solution despite increases in the negative pressure of the dialysate solution being pumped. This surprising improvement is due to several distinct, interrelated pump characteristics, as discussed below.

First, relative to the above-described prior art pump, the pump of this invention comprises four rollers mounted on the pump assembly base member, as compared to three rollers in the prior art pump. The provision of an additional roller tends to decrease the length of the pumping section segment between adjacent rollers relative to the prior art system, so that the pumping section segments between adjacent rollers are correspondingly "stiffer" and have a higher resistance to deformation, whereby negative pressure forces collapse these tubing segments to only a low extent relative to the tubing segments in the prior art pumping system.

Second, the rollers employed in the pump of this invention have a generally convex surface profile, as adapted for only partial closure of the tubing at the points of compression by the rollers. By such roller configuration, the pump of the present invention, in contrast to the prior art pump employing rollers with a flat surface profile, avoids total occlusion of the tubing section at the point of compression with the roller, such as would result in excessive flattening of the tube segments between adjacent rollers and make these tubing segments disproportionately more susceptible to deformation by negative pressure forces. In this regard, the generally convex surface profile of the roller tends to localize the deformation of the tubing cross-section to a narrow region closely adjacent the point of compression with the roller, in contrast with the prior art system in which the flat surfaced rollers and total occlusion at the points of compression with the rollers results in substantial flattening of the tubing segments for an appreciable distance away from the point of contact with the roller.

Third, the pump means of the present invention employ a flexible resilient tubing pumping section which has a length which is generally greater than the length employed in the prior art pumping system. This difference in length reflects a corresponding difference in tensioning levels of the tubing sections extended around the rollers of the pump head assembly in the respective systems. Tubing pumping section lengths are generally associated with specific tensional characteristics of the tubing section stretched around the pump head rollers, with shorter tubing pumping section lengths generally being associated with higher tension levels and longer tubing pumping section lengths generally being associated with lower tension levels. The prior art pumping system employs relatively shorter pumping segment lengths, as associated with the relatively high tension levels which are employed to facilitate total occlusion of the tubing section at the point of contact with the rollers. By contrast, the pump of the present invention employs a relatively longer tubing pumping segment length, as associated with a relatively lower tension level to provide only partial occlusion or closure of the tubing at the points of compression by the rollers.

More generally, the specific range of lengths of the flexible resilient tubing pumping section in accordance with this invention is associated with the objective of operating at a comparatively lower pump head rotational speed than the above-described prior art pump in order to provide a relatively longer operating life for the tubing pumping section, by reducing the extent of contact between the tubing and the pump head assembly rollers, and to achieve quieter operation. To realize the objective of operating at low rotational speed, while accommodating the size and weight requirements associated with portability of the hemodialysis system, the roller spacing (distance between the roller axis and the pump head assembly base member fixed axis) was increased to the maximum extent practicable consistent with drive means power consumption and torque considerations, thus establishing the tubing length requirements in accordance with the present invention.

Under the foregoing structural characteristics, the tubing pumping segment in the pump means of the present invention is only partially occluded at the points of compression by the rollers. Such partial occlusion of the tubing section permits the output flow rate of dialysate solution from the pump to be maintained substantially constant despite increases in the negative pressure of the dialysate solution being pumped. In operation, as negative pressure of the dialysate solution is increased, an increased collapsing pressure is exerted on the outer wall surface of the tubing pumping section which to some extent deforms the segments of the pumping section between adjacent rollers and reduces the volume of these tubing segments, as also occurs in the above-described prior art pumping system. Nonetheless, in the pump of the present invention, deformation of the tubing cross-section as a result of the increased negative pressure differential also occurs in the tubing at the points of compression by the rollers, thereby resulting in increased occlusion of the tubing at such points of compression. The increased degree of occlusion at the points of compression correspondingly reduces the level of backflow from the portion of the tubing section downstream from the roller to the portion of the tubing section upstream of the roller, so that pumping efficiency is increased. The beneficial effect of increased occlusion as enhancing pumping efficiency at higher negative pressure levels has been found to compensate for the reduction in volume of the tubing segments between adjacent rollers as a result of increasing negative pressure, so that these opposing effects are substantially balanced to provide a substantially constant output flow rate of dialysate solution from the pump despite increase in negative pressure of the dialysate solution being pumped.

Under the present invention, the peristaltic pumping section of tubing must be both flexible and resilient so that the tubing even though under continuously varying tensional and compressive load conditions, does not tend to fatigue and crack in use and so that the tubing quickly reacquires its undeformed shape and dimensions after the direct bearing of roller compression on the tubing is released as the roller moves along the length of the tubing. Tubing pumping sections formed of silicon elastomers and particularly silicon elastomers of 40-60 durometer have been found to satisfy the foregoing requirements and to be particularly useful in the practice of this invention.

In the practice of the present invention, the rollers mounted on the pump head assembly have a generally convex surface profile with a maximum diameter of between 0.25 and 0.75 inch. At diameter values below 0.25 inch, it becomes increasingly difficult to achieve only partial occlusion of the tubing pumping segment, such as required in accordance with the present invention.

If the roller diameter exceeds about 0.75 inch, an excessive amount of tubing is partially occluded when the roller engages the tubing pumping section, thereby undesirably lowering the instantaneous volumetric pumping capability of the pump means and hence the pumping efficiency of the pump means.

The present invention requires a radial distance, as measured between a given roller axis and the pump head assembly base member fixed axis, of from 0.50 to 1.50 inches. The reasons for such limits are complementary to the reasons discussed above for the roller diameter limits. If the radial distance is less than about 0.50, the rotational speed requirements for maintaining suitable output flow rates of dialsyate solution become excessive; in addition, at radial distance values of less than about 0.50, an excessive amount of tubing is partially occluded when the roller engages the tubing pumping section, thereby undesirably lowering the instantaneous volumetric pumping capability of the pump means and hence the pumping efficiency of the pump means. On the other hand, if the radial distance is greater than about 1.50 inches, the unsupported lengths of tubing between adjacent rollers tend to be too long relative to the size of the rollers contacting the tubing, so that the unsupported lengths of tubing are disproportionately more susceptible to deformation by pressure differential forces associated with higher dialysate solution negative pressure levels.

The flexible resilient tubing pumping section under the present invention must have a length, as measured longitudinally along the tubing between the anchored end segments thereof, of from 6.75 to 11.0 inches, a wall thickness of from 0.07 to 0.125 inch, and an internal diameter of from 0.18 to 0.35 inch. As the pumping section tubing length, e.g., as measured longitudinally along the tubing between the coupling members 208 and 209 in the illustrated FIG. 4 embodiment, decreases below about 6.75 inches, a point is reached where pump head rotational speed requirements become excessively high, with correspondingly shortened tubing life, and it may be difficult to extend the tubing around the pump head assembly with adequately low tension for only partial occlusion at the points of contact of the tubing with the rollers. At length values above about 11.0 inches, the length of the tubing section tends to overmatch the dimensions of the pump head assembly, and it becomes disproportionately more difficult to tensionally extend the tubing pumping section around the pump head rollers with sufficient occlusion of the tubing at the points of compression by the rollers. A tubing wall thickness of at least 0.07 inch is necessary to insure the leak-tight integrity of the tubing pumping section, which is subjected to continuous and rapid swings of tensional extension and relaxation such as tend to unduly fatigue and rupture tubing sections of lesser thickness. At tubing thicknesses above about 0.125 inch, the pumping section tends to become too rigid for adequate and proper compression by the rollers. If the internal diameter of the tubing pumping section decreases below about 0.18 inch, there tends to be an improper match between the tubing size and the roller size requirements, with the result that an excessive volume of tubing is partially occluded, with corresponding reduction in pumping efficiency for the system. On the other hand, at tubing internal diameter values above 0.25 inch, under the aforementioned wall thickness range of from 0.07 to 0.125 inch, the tubing section tends to be excessively deformable at higher dialysate solution negative pressure values, with consequent adverse affect on pumping efficiency at such higher dialysate solution negative pressure values.

Finally, the peristaltic dialysate pump means in the present invention include drive means coupled to the pump head assembly of the dialysate solution pump for rotation thereof at a speed in the range of from 150 to 400 rpm. These limits are set by the dialysate solution flow rate requirements of the hemodialysis system. To obtain suitably high dialyzing efficiency, the flow rate of the dialysate solution in the dialysate solution flow circuit in the hemodialysis system should be on the order of 450–550 ml/min. The rotational speed of the dialysate solution pump drive means is a function of the radial distance measured between a given roller axis and the pump head assembly base member fixed axis. This is because the liquid pumping volumes in the tubing segments between adjacent rollers are a function of this radial distance, so that as the radial distance decreases, the rotational speed of the drive means for the pump must increase to maintain dialysate solution flow rate in the dialsyate solution flow circuit at the desired level. For the aforementioned radial distance range of 0.50 to 1.50 inches, the pump drive means rotational speed for maintaining dialysate solution flow rate in the desired range would progressively decrease from about 400 rpm at a radial distance of 0.50 inch to about 150 rpm at a radial distance of 1.50 inches.

In preferred practice, the flexible resilient tubing pumping section of the pump of this invention has a length of 7 to 10 inches, and the ratio of the wall thickness to the internal diameter of the flexible resilient tubing pumping section is in the range of from 0.35 to 0.40 in order to avoid excessive load on the dialysate solution pump drive means while providing a tubing pumping section with adequate resistance to deformation with increase in dialysate solution negative pressure.

FIG. 5 is a sectional elevational view of the dialysate solution pump and associated drive means as employed in the FIG. 2 hemodialysis system and as shown in plan view in FIG. 4 herein. System elements in FIG. 5 are numbered correspondingly with respect to FIG. 4.

As shown in FIG. 5, the pump head assembly is mounted in enclosure 200 into which the dialysate solution inlet line 114 passes, terminating at the previously described fitting 204 comprising flange portion 206. The rotatable pump head assembly includes a base member 201 positioned for rotation about a fixed axis with a plurality of circumferentially spaced-apart rollers 202a and 202c mounted thereon for independent rotation about respective axes parallel to the base member fixed axis. The base member 201 includes the horizontally extending peripheral portion 220 on which the rollers are mounted, as for example by suitable screw or bolt means. The rollers are retained in position at their upper ends by cover plate member 221, to which the rollers may also be suitably joined as by screw or bolt means which allow independent rotation of the rollers about their own axes. The rollers 202a and 202c each have a generally convex surface profile to provide for only partial closure of the tubing at the points of compression by the rollers. The rollers have outwardly extending flanged end portions 222 and 223 to retain the tubing pumping section in place on the roller surfaces during operation.

The base member 201 of the pump head assembly has a raised spindle porton 203 which is disposed on the shaft 224 of electric motor drive means 225, to which power is supplied by electrical leads 226 and 227.

FIG. 6 is a graph of dialysate solution flow rate (pump output), in ml/min., plotted as a function of negative pressure, in mm Hg, for a dialysate solution pump according to U.S. patent appliction Ser. No. 720,672 (curve A) and a dialysate solution pump according to the present invention (curve B). The dialysate solution pump for curve A was constructed in accordance with the teachings of U.S. patent application Ser. No. 720,672 and had three rollers, each having a diameter of 0.50 inch, with a radial distance between the roller axis and the base member fixed axis of 0.75 inch. The flexible resilient tubing pumping section for the prior art pump had a length of 6.625 inches, an inner diameter of 0.187 inch and outer diameter of 0.3125 inch. Drive means were coupled to the pump head assembly for rotation thereof at a speed of 400 rpm.

The pump for curve B constructed in accordance with the present invention had four rollers, each having a generally convex surface profile with a maximum diameter of 0.375 inch, with a radial distance between the roller axis and the base member fixed axis of 0.8125 inch. The flexible resilient tubing pumping section for this pump had a length of 8.75 inches, a wall thickness of 0.094 inch, and an internal diameter of 0.25 inch. Drive means were coupled to the pump head assembly for rotation thereof at a speed of 200 rpm.

As shown by the respective curves in FIG. 6, the dialysate solution pump of the present invention (curve B) exhibited a relatively constant output flow rate, varying only between 490 and 570 ml/min, over a negative pressure range of from 0 to 350 mm Hg. By contrast, the prior art pump (curve A) evidenced a drastic reduction in dialysate solution output flow rate, from about 560 ml/min at 0 mm Hg negative pressure down to about 150 ml/min at 300 mm Hg negative pressure. As discussed earlier herein, the total occlusion of the tubing pumping section at the points of compression by the rollers together with the roller spacing and tubing dimensions in the prior art pumping system causes extensive flattening of the tubing segment portions between adjacent rollers, such that increases in negative pressure severely collapse the tubing segments between adjacent rollers, thereby causing the sharp decline in pump output flow rate with increasing negative pressure as shown in the graph in FIG. 6. By contrast, the output flow rate of dialysate solution from the pump of this invention lies within a comparatively narrow band of values over the entire negative pressure range, as shown by curve B. As shown, curve B exhibits a comparatively shallow decrease in flow rate out to about 60 mm Hg, followed by a gradual rise in output flow rate to about 200 mm Hg and a comparatively shallow decrease above 200 mm Hg negative pressure. These various segments of curve B may be explained in terms of the degree of occlusion and extent of tubing deformation over the successive ranges of negative pressure. From 0 to 60 mm Hg negative pressure, the increasing negative pressure results in a progressively increasing low level of deformation of the tubing segments between adjacent rollers so that dialysate solution flow rate from the pump slowly decreases over this negative pressure range. Above 60 mm Hg negative pressure, the increasing negative pressure levels cause a progressively increasing degree of occlusion of the tubing at the points of compression by the rollers, resulting in an increase in pumping efficiency which more than counterbalances the decrease in liquid volume in the tubing segments between adjacent rollers due to increasing deformation with increasing negative pressure, so that the dialysate solution output flow rate from the pump progressively increases to a value of about 200 mm Hg negative pressure. Above such negative pressure level, the effect of decrease in liquid volumes in the tubing segments between adjacent rollers of the pumping means tends to predominate slightly over the improvement in pumping efficiency associated with increasing levels of partial occlusion of the tubing at the points of compression by the rollers with increasing negative pressure, so that the output flow rate curve shows a shallow decline. Despite these changes in slope over the negative pressure range, curve B exhibits only a 7½ percent variation from the median flow rate of 530 ml/min over the full range of negative pressure of 0 to 350 mm Hg. By contrast, the prior art pumping system exhibited a sharp drop in dialysate solution output flow rate of approximately 73 percent over the negative pressure range of 0 to 300 mm Hg negative pressure. The curves in FIG. 6 strikingly show the improvement which is obtained with the pumping means of the present invention relative to the dialysate pumping means of the prior art.

Figure 7:
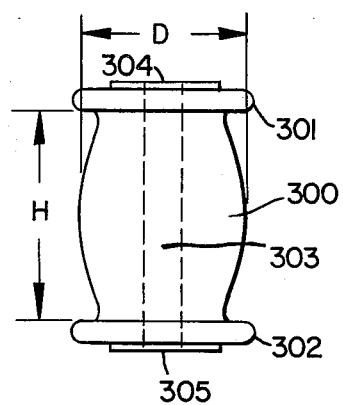
FIG. 7 is an elevational view of a roller configuration such as may be usefully employed in the dialysate solution pump of FIGS. 4-5.

FIG. 7 shows an embodiment of a roller such as may be suitably employed in the practice of the present invention. The roller has a bearing surface 300, against which the tubing is engaged in the manner shown in FIG. 4. Bearing surface 300 has a generally convex surface profile, for only partial closure of the tubing at the points of compression by the roller. As used herein "a generally convex surface profile" means that the surface contour of the bearing surface taken in a radial plane passing through the axis of rotation of the roller is generally convex in shape, with the roller diameter at the midsection of the roller 300a being greater than the roller diameter at the end portions 300b and 300c of the roller bearing surface. The roller has a maximum diameter D, as measured in a plane perpendicular to the axis of rotation of the roller, of from 0.25 to 0.75 inch, and as for example 0.375 inch. The height H of the roller for the aforementioned maximum diameter D of the roller is approximately 0.593 inch. As shown, the roller is provided with flanged end segments 301 and 302, which serve to retain the tubing in place on the roller bearing surface 300. The roller is provided with an axle member 303 having a longitudinal shaft portion which extends through an appropriately sized central passage through the roller body. The axle member 303 comprises flattened end portions 304 and 305 which retain the roller in place on the longitudinally extending shaft portion of the axle member. In this fashion, the rollers may be mounted on the pump head assembly base member for independent rotation about roller axes parallel to the base member fixed axis, as for example by bonding or mechanically joining the flattened end portion 305 of the axle member to the pump head assembly base member. In practice, the rollers may be formed of any suitable material of construction; however, polymeric materials of construction having a low coefficient of surface friction are preferred, in order to minimize abrasion of the tubing by the roller bearing surface in operation.

Figure 8:
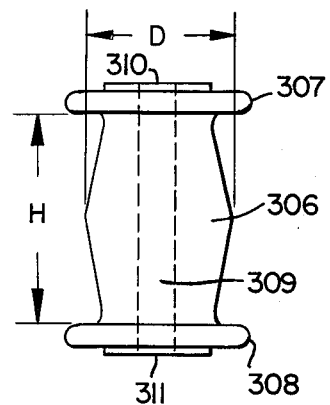
FIG. 8 is an elevational view of another roller configuration such as may be usefully employed in the dialysate solution pump of FIGS. 4-5.

FIG. 8 shows an alternative embodiment of a roller such as may be employed in the practice of the invention. This roller has a bearing surface 306 with a generally convex surface profile. The roller comprises flanged end portions 307 and 308 to retain the tubing in position on the bearing surface in operation. Axle member 309 extends through a central passageway in the roller body and comprises flattened end portions 310 and 311 to retain the roller in position on the shaft portion of the axle member. The roller has a maximum diameter D of between 0.25 and 0.75 inch. The roller of FIG. 8 differs from that shown in FIG. 7 in that the former has a bearing surface contour formed by a bilinear taper convex surface profile, while the latter features a smoothly curved convex surface profile. Both roller embodiments provide a generally convex bearing surface profile, for only partial closure of the tubing at the points of compression by the roller.

Although preferred embodiments of the invention have been described in detail, it will be appreciated that other embodiments are contemplated, only with modifications of the disclosed features, as being within the scope of the invention.

What is claimed is:

1. Peristaltic pump means for use in hemodialysis apparatus, comprising a rotatable pump head assembly including a base member positioned for rotation about a fixed axis with four circumferentially spaced apart rollers mounted thereon for independent rotation about respective axes parallel to the base member fixed axis; flexible resilient tubing through which a negative pressure fluid is pumped; means for anchoring end segments of the flexible resilient tubing such that the tubing is tensionally extended around the pump head assembly, being simultaneously engaged and compressed by at least two of said circumferentially spaced apart rollers, said rollers being mounted for longitudinal movement of the points of compression along the tubing during rotation of said pump head assembly to advance fluid through said tubing; each of said four rollers having a generally convex surface profile, for only partial closure of the tubing at the points of compression by said rollers, and circumferentially spaced 90° apart from adjacent rollers; said flexible resilient tubing having a length, as measured longitudinally along the tubing between the anchored end segments thereof, of from 6.75 to 11.0 inches, a wall thickness no greater than 0.125 inch, and an internal diameter no greater than 0.35 inch; and drive means coupled to said pump head assembly for rotation thereof.

2. The invention of claim 1 wherein said peristaltic pump means is mounted for service in a unitary enclosure dialysis module.

3. The invention of claim 1 wherein the flexible resilient tubing is formed of a silicone elastomer.

4. The invention of claim 3 wherein said silicone elastomer has a durometer value of from 40 to 60.

5. Hemodialysis apparatus for treatment of blood to remove waste impurities therefrom, including: dialyzer means through which waste impurity-containing blood and a dialysate solution are passed in indirect mass transfer dialyzing relationship for transfer of said waste impurities from said blood to said dialysate solution; means for transferring waste impurity-containing blood from a patient to said dialyzer means including a flexible resilient tubing pumping section through which blood is pumped and means for returning waste impurity-depleted blood to said patient forming a blood flow circuit; means for transferring dialysate solution from a negative pressure dialysate solution source to said dialyzer means and means for discharging waste impurity-enriched dialysate solution from said dialyzer means forming a dialysate solution flow circuit including a flexible resilient tubing pumping section through which dialysate solution is pumped; peristaltic blood pump means disposed in said blood flow circuit and peristaltic dialysate pump means disposed in said dialysate solution flow circuit each pump means comprising a rotatable pump head assembly including a base member positioned for rotation about a fixed axis with a plurality of circumferentially spaced apart rollers mounted thereon for independent rotation about respective axes parallel to the base member fixed axis, at least said peristaltic dialysate pump means having four spaced apart rollers mounted on the base member thereof; means for anchoring the end segments of the flexible resilient tubing pumping section in said blood flow circuit and means for anchoring the end segments of the flexible resilient tubing pumping section in said dialysate solution flow circuit such that the tubing in each circuit is tensionally extended around the pump head assembly of a respective one of said peristaltic pump means and is simultaneously engaged and compressed by at least two of said circumferentially spaced apart rollers of the respective peristaltic pump means, the rollers of each peristaltic pump means being mounted for longitudinal movement of the points of compression along the associated tubing during rotation of said pump head assembly to advance fluid through said tubing; each of said four rollers in at least the peristaltic dialysate pump means having a generally convex surface profile, for only partial closure of the tubing at the points of compression by the rollers, with a maximum diameter between 0.25 and 0.75 inch and circumferentially spaced 90° apart from adjacent rollers with a radial distance between the roller axis and said base member fixed axis of from 0.50 to 1.50 inches; said flexible resilient tubing pumping section in the dialysate flow circuit having a length, as measured longitudinally along the tubing between the anchored end segments thereof, of from 6.75 to 11.0 inches, a wall thickness of from 0.07 to 0.125 inch, and an internal diameter of from 0.18 to 0.35 inch; and drive means coupled to the pump head assembly of the peristaltic dialysate pump means for rotation thereof at a speed in the range of from 150 to 400 rpm.

6. Apparatus according to claim 5 wherein a portion of said dialysate solution flow circuit, including said peristaltic dialysate pump means, is disposed in a unitary enclosure dialysis module, with said dialysate solution flow circuit portion being alternatively and detachably interconnectable with either a dialysate solution proportioning system, for single-pass flow of dialysate solution through said dialysate solution flow circuit, or a dialysate solution supply container, for batch recirculation of dialysate solution through said dialysate solution flow circuit.

7. Apparatus according to claim 6 wherein said proportioning system comprises means for providing a continuous flow of water at elevated temperature to proportioning means wherein said water and a dialysate concentrate are mixed together in a predetermined ratio to form said dialysate solution, said means for providing a continuous flow of water at elevated temperature including water source means and means for heating water from said source means to said elevated temperature, and deaeration means for removing soluble gases from the heated water prior to passage thereof to said proportioning means, said deaeration means including:

(a) a first reservoir receiving heated water from said heating means, having venting means to permit gases desolubilized from said water in said heating to disengage from the heated water to form partially deaerated water;

(b) a vacuum pump;

(c) a conduit joining said first reservoir with an inlet of said vacuum pump for passage of said partially deaerated water from said first reservoir to said vacuum pump;

(d) adjustable flow restriction means disposed in said conduit for reduction in pressure of the partially deaerated water passed through said conduit to further desolubilize gases therefrom and form lower pressure water with desolubilized gas dispersed therein;

(e) a conduit joined at one end to an outlet of said vacuum pump for discharging higher pressure water with desolubilized gas dispersed therein from said pump;

(f) a second reservoir joined to the other end of said conduit (e) for receiving discharged higher pressure water therefrom, having venting means to permit said desolubilized gas to disengage from said higher pressure water to form finally deaerated water; and (g) means for transferring said finally deaerated water from said second reservoir to said proportioning means, wherein said proportioning means are joinable to said dialysate solution flow circuit to supply dialysate solution to same.

8. Apparatus according to claim 7 wherein said deaeration means further include: overflow discharge means for maintaining liquid level in said first reservoir below a predetermined level; and a conduit joining said first reservoir with said second reservoir for recirculation of a portion of said finally deaerated water from said second reservoir to said first reservoir to enhance removal of soluble gases by said deaeration means.

9. Apparatus according to claim 6 wherein the remainder of said dialysate solution flow circuit is detachably coupled to said flexible resilient tubing pumping section thereof.

10. Apparatus according to claim 7 wherein said proportioning system is mounted for service in a unitary enclosure as a dialysate solution supply module.

11. Apparatus according to claim 5 wherein said dialysate flow circuit forms a closed loop with said dialysate solution source for batch recirculation of said dialysate solution through said dialyzer means.

12. Apparatus according to claim 5 wherein said dialysate solution source comprises proportioning means for continuously mixing water from a source of same with dialysate concentrate to form said dialysate solution and wherein said dialysate solution is flowed through said dialysate solution flow circuit in single pass flow.

13. Apparatus according to claim 5 wherein said dialysate solution flow circuit includes a portion upstream of said dialyzer means with which are associated: means for heating said dialysate solution; means for sensing the temperature of said dialysate solution disposed downstream from said heating means and for adjusting the rate of heating of said dialysate solution by said heating means in response to said temperature sensing to maintain a predetermined dialysate solution temperature level; and means for sensing the electrolytic conductivity of said dialysate solution.

14. Apparatus according to claim 13 wherein means for detecting blood leakage are associated with a dialysate solution flow circuit portion downstream of said dialyzer means.

15. Apparatus according to claim 13 comprising: means for converting said dialysate solution temperature sensing into a transmittable signal; means for transmitting said temperature sensing signal; visual display means coupled with said temperature sensing means by said signal transmitting means for indication of said sensed dialysate solution temperature; means for converting said dialysate solution electrolytic conductivity into a transmittable signal; means for transmitting said electrolytic conductivity sensing signal; and visual display means coupled with said electrolytic conductivity sensing means by said conductivity signal transmitting means for indication of said sensed dialysate solution electrolytic conductivity.

16. Apparatus according to claim 5 wherein said dialysate solution flow circuit has associated therewith in a portion of said circuit upstream of said dialyzer means: (a) means for heating said dialysate solution; (b) means for sensing the temperature of said dialysate solution and adjusting the rate of heating of said dialysate solution by said heating means in response to said temperature sensing to maintain a predetermined dialysate solution temperature level; (c) means for converting said dialysate solution temperature sensing into a transmittable signal; (d) means for transmitting said temperature sensing signal; (e) visual display means coupled with said temperature sensing means by said signal transmitting means for indication of said sensed dialysate solution temperature; (f) means for sensing the electrolytic conductivity of said dialysate solution; (g) means for converting said dialysate solution electrolytic conductivity into a transmittable signal; (h) means for transmitting said electrolytic conductivity sensing signal; and (i) visual display means coupled with said electrolytic conductivity sensing means by said conductivity signal transmitting means for indication of said sensed dialysate solution electrolytic conductivity; and a portion of said dialysate solution flow circuit downstream of said dialyzer means has associated therewith (j) means for detecting blood leakage; wherein said dual peristaltic pump means, anchoring means, pump drive means, and said means (a)-(j) associated with said dialysate solution flow circuit are mounted for service in a unitary enclosure.

17. Apparatus according to claim 5 wherein said flexible resilient tubing pumping section in the dialysate solution flow circuit has a length of 7 to 10 inches.

18. Apparatus according to claim 5 wherein the ratio of said wall thickness to said internal diameter of said flexible resilient tubing pumping section in the dialysate solution flow circuit is in the range of from 0.35 to 0.40.

* * * * *